United States Patent
Trapp et al.

(10) Patent No.: US 8,978,438 B2
(45) Date of Patent: Mar. 17, 2015

(54) METHOD FOR START-UP OF A MEASURING DEVICE

(75) Inventors: Thilo Trapp, Aliso Viejo, CA (US);
Torsten Pechstein, Radebeul (DE)

(73) Assignee: Endress + Hauser Conducta Gesellschaft für Mess-und Regeltechnik mbH + Co. KG, Gerlingen (DE)

(*) Notice: Subject to any disclaimer, the term of this patent is extended or adjusted under 35 U.S.C. 154(b) by 372 days.

(21) Appl. No.: 13/324,066

(22) Filed: Dec. 13, 2011

(65) Prior Publication Data
US 2012/0144894 A1    Jun. 14, 2012

(30) Foreign Application Priority Data
Dec. 14, 2010   (DE) .......................... 10 2010 063 033

(51) Int. Cl.
  *G01N 33/48*      (2006.01)
  *G01N 35/00*      (2006.01)
  *G01N 27/416*     (2006.01)

(52) U.S. Cl.
  CPC ...... *G01N 35/00693* (2013.01); *G01N 27/4165* (2013.01); *G01N 35/00712* (2013.01)
  USPC ........................................................... 73/1.02

(58) Field of Classification Search
  USPC ........................................................... 73/1.02
  See application file for complete search history.

(56) References Cited

U.S. PATENT DOCUMENTS

| | | | | |
|---|---|---|---|---|
| 6,025,169 | A * | 2/2000 | Nakamura et al. | 435/115 |
| 7,961,327 | B1 * | 6/2011 | LoPresti et al. | 356/436 |
| 2007/0168145 | A1 | 7/2007 | Beyer | |
| 2009/0233334 | A1 * | 9/2009 | Hildinger et al. | 435/71.1 |

FOREIGN PATENT DOCUMENTS

| | | |
|---|---|---|
| DE | 10214713 A1 | 10/2003 |
| DE | 10254444 A1 | 6/2004 |
| DE | 10256649 A1 | 6/2004 |
| DE | 102004004031 A1 | 8/2005 |
| DE | 60317699 T2 | 10/2008 |
| DE | 10 2008043135 A1 | 4/2010 |
| DE | 102009028794 A1 | 2/2011 |
| EP | 2065701 A2 | 6/2009 |
| WO | WO 03/082469 A2 | 10/2003 |
| WO | WO 2004/029193 A1 | 4/2004 |
| WO | WO 2004/051246 A3 | 6/2004 |
| WO | WO 2009/059645 A1 | 5/2009 |

* cited by examiner

Primary Examiner — Paul West
(74) Attorney, Agent, or Firm — Bacon & Thomas, PLLC

(57) ABSTRACT

A method for start-up of a measuring device, which is embodied to monitor by means of at least one measuring transducer in contact with the interior of a process container, especially of a single-use container, a measured variable of a medium contained in the process container, wherein, for ascertaining a measured value, at least one measurement signal of the measuring transducer is mapped to a measured value of the measured variable according to a predetermined characteristic curve, wherein the method includes: introducing a process medium into the process container; bringing the measuring transducer in contact with the process medium; and performing a one-point calibrating of the measuring device based on a measurement signal registered by the measuring transducer in the process medium or a measured value derived therefrom based on the characteristic curve.

11 Claims, 2 Drawing Sheets

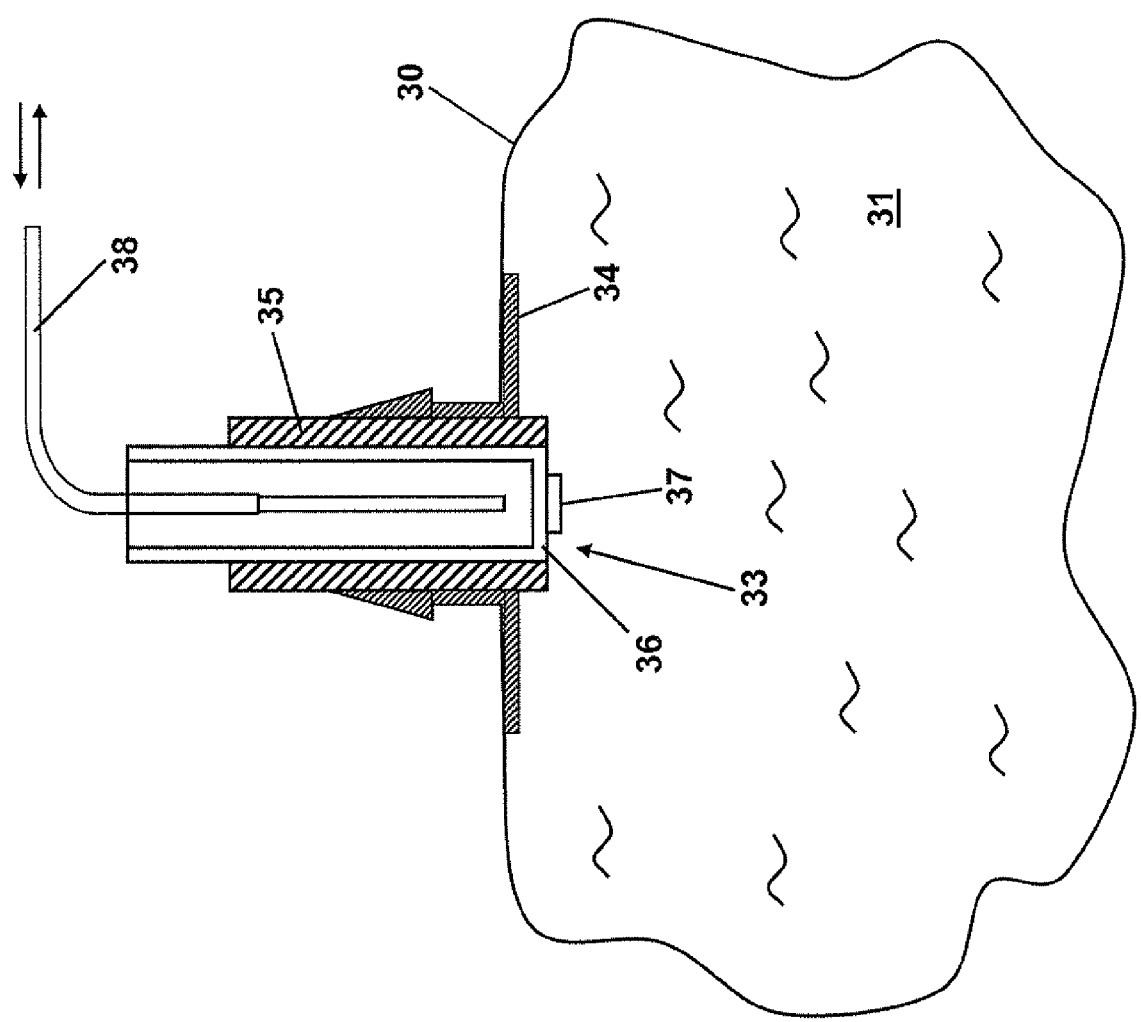

METHOD FOR START-UP OF A MEASURING DEVICE

TECHNICAL FIELD

The invention relates to a method for start-up of a measuring device, which is embodied to monitor by means of at least one measuring transducer in contact with the interior of a process container, especially of a single-use container, a measured variable of a medium contained in the process container, wherein, for ascertaining a measured value, at least one measurement signal of the measuring transducer is mapped to a measured value of the measured variable according to a predetermined characteristic curve.

BACKGROUND DISCUSSION

Pharmaceutical, chemical, biological, biochemical or biotech processes are, in increasing measure, performed in single-use containers (also referred to as disposables, or disposable bioreactors) as process containers. Such single-use containers can be, for example, flexible containers, e.g. bags, tubes or fermenters, or bioreactors. Bioreactors or fermenters frequently possess supply, and drain, lines, which can, for example, be embodied as tubes. In the supply, and drain, lines, also rigid tubular pieces can be inserted. After terminating a process, single-use containers can be disposed of. In this way, complex cleaning- and sterilization methods are avoided. Especially, through the use of single-use containers, the risk of cross contamination is prevented and, therewith, process safety is increased.

The processes performed in single-use containers proceed in a closed system, i.e. without connection to the environment outside the single-use containers. Since, frequently, sterile conditions are required, single-use container must be sterilized before introducing the process media. Frequently used for this purpose in biochemical, biological, biotechnological and pharmaceutical applications is gamma radiation. Also, in processes proceeding in a single-use fermenter or single-use reactor, the penetration of impurities, especially germs, from the environment into the interior of the process container must be prevented, in order not to degrade or corrupt the process flow.

In order to monitor or to check the processes, it can be necessary to measure physical or chemical, measured variables of the media contained in the process container. The measured variables to be monitored can be, for example, temperature, pH-value, cell density, optical transmission or a concentration of a chemical substance, for example, a certain kind of ion, a certain element or a certain compound, e.g. the content of dissolved oxygen or CO2. In biotechnological methods, important measured variables can include, moreover, so-called feeding material parameters, e.g. the glucose-, glutamate- or lactose content of the process medium, or metabolism parameters of the microorganisms applied in the method.

An opportunity for measuring at least some of these measured variables lies in the application of optical sensors. For example, sensorially active surfaces (technical term: optical sensor spots) capable of being read out optically can be arranged in the container. These can be accessed contactlessly externally through a window. For determining turbidity or cell density, likewise measurements can be performed externally through sending measuring radiation through a window or a transparent container wall and registering the radiation scattered and/or transmitted in the process medium.

Alternatively, or supplementally, to optical sensors, also electrochemical, especially potentiometric, sensors can be used, especially for determining the pH-value or an ion concentration in the process medium. Also amperometric sensors can be applied for determining the oxygen content or the CO2-content, as well as conductivity sensors, which work according to a conductive, or inductive, principle.

While in the case of optical sensors, at most, one sensorially active area, not, however, a measurement circuit or other components of the measuring transducer, come in contact with the process medium, it is, in the case of the named non-optical sensors, as a rule, required, to immerse the measuring transducer at least partially into the process medium and to lead out via wires a primary signal registered in the medium, or a signal derived therefrom, from the interior of the process container. Correspondingly, at least the part the non-optical sensors provided for introduction into the process container must be sterilized, just as the process container itself, while in the case of optical sensors, at most, the optically readable, sensorially active area must be sterilized.

In published international patent application WO 2009/071829 A2 and German Offenlegungsschrift DE 10 2006 005 533 A1, complex mechanical coupling systems are described, which enable sterile introduction of an externally sterilized sensor into a single-use container.

In order to avoid such complex coupling systems, the potentiometric probe can be installed via a connection fixedly in the process container, before the sterilization of the process container (for example, by irradiation with gamma radiation) and remain therein for the duration of storage and application. While the actual use time of the single-use container will amount to only few weeks, storage times can be in the order of magnitude of one or more years.

Electrochemical sensors, for example, potentiometric sensors as pH-glass electrodes or ion-selective electrodes, or amperometric sensors, e.g. for dissolved oxygen measurement, have sensitive membranes and one or more inner electrolytes, which, over the storage time of the sensor, can age, thus leading to a drift of the sensor and possibly even to degradation of the accuracy of measurement of the sensor.

SUMMARY OF THE INVENTION

An object of the invention is to provide a method enabling a measuring device with a measuring transducer to operate in the previously described applications with sufficient accuracy of measurement and measurement quality.

This object is achieved by a method for start-up of a sensor, which is embodied to monitor by means of at least one measuring transducer in contact with the interior of a process container, especially of a single-use container, a measured variable of a medium contained in the process container, wherein, for ascertaining a measured value, at least one measurement signal of the measuring transducer is mapped to a measured value of the measured variable according to a predetermined characteristic curve, wherein the method includes:

introducing a process medium into the process container;
bringing the measuring transducer in contact with the process medium; and
performing a one-point calibrating of the measuring device based on a measurement signal registered by the measuring transducer in the process medium or a measured value derived therefrom based on the characteristic curve.

Since a one-point calibrating is performed at start-up, on the one hand, a review of the sensor can be performed as regards its functionality. On the other hand, the one-point calibrating assures a sufficient accuracy of measurement, since, in the case of little chemically, mechanically or thermally loaded sensors, such a one-point calibrating is frequently sufficient.

The term, calibrating, is frequently used, especially in pH-measuring, with a meaning other than generally understood. In general one means with 'calibrating' the reviewing of the display of a measuring device with a standard; the deviation between true value and display value is detected. The correcting of the display value to the true value is referred to as adjusting. Calibrating, in the case of the pH-sensor represents, strictly, an adjusting. Since the term calibrating is commonly used in electrochemistry, it is also used here.

The measuring device includes a data processing unit, in whose memory the characteristic curve is stored, and which maps measuring signals of the measuring transducer to measured values based on this characteristic curve. For example, the measuring transducer can be embodied as a sensor offset from the data processing unit and connected with the data processing unit (embodied as a measurement transmitter) via a cable connection for the transmission of signals, wherein the sensor and the therewith connected measurement transmitter form a measuring device. A large number of other variants of measuring device construction are possible, for example, the sensor can comprise a measurement circuit, which processes the measurement signal and outputs the processed measurement signal to the measurement transmitter.

Alternatively, sensor and measurement transmitter can be arranged together in a single housing.

The one-point calibrating can comprise steps as follows:
registering by means of the measuring transducer a measured value of the measured variable of the process medium as a current calibration measured value,
updating the predetermined characteristic curve (according to which a measurement signal of the measuring transducer is mapped to a measured value) stored in a memory associated with the measuring transducer based on the current calibration measured value. The memory associated with the measuring transducer can be arranged in the sensor itself or in a superordinated unit, e.g. a measurement transmitter, connected with the sensor for the data transmission.

The characteristic curve can be a straight line, wherein, based on the current calibration measured value, in the case of the one-point calibrating, the zero-point (axial intercept) of the straight line is corrected.

In a biotech process, in which microorganisms are applied for the manufacture of a desired product, the process medium is preferably a feeding medium, whose chemical composition and/or whose value of the measured variable to be monitored by the measuring transducer is known. The value of the measured variable of the feeding medium can have been ascertained, for example, by way of an earlier performed, reference measurement. Feeding media are subject to strict specifications as regards many measured variables, e.g. the pH-value or the content of certain chemical compounds. The feeding solutions are, for example, exactly specified as regards pH-value tolerances of 0.1 to 0.05 pH. Therewith in the case of application of the feeding medium for performing a one-point calibrating, for example, of a pH-sensor, no reference measurement need be performed, but, instead, the known, specified value of the measured variable to be monitored, thus, for example, the pH-value, can be used.

The measured variable can be, besides the pH-value, also the conductivity or the concentration of a certain substance. For example, involved can be a concentration of a dissolved gas or the concentration of a type of ion. The concentration of a certain substance can especially also be a feeding material parameter, e.g. the concentration of a substance relevant in biotechnological systems, such as e.g. glycol, glucose, glutamate, lactate or a concentration of other substances relevant for the biotechnological process to be monitored, e.g. certain proteins, pheromones or hormones.

The process container can be a single-use container for application in a biotechnological process, especially a flexible container, a bag-fermenter, a hose, or a tubular connection.

In an embodiment, the measuring transducer can be a potentiometric sensor with a measuring half cell and a reference half-cell, wherein the sensor has an immersion region, which includes a membrane of a measuring half cell sensitive for the measured variable to be monitored and a bridge, especially a diaphragm, for providing an electrolytic contact between the reference half-cell and the process medium. In this embodiment, the measuring transducer is brought in contact with the process medium by immersing the immersion region in the process medium.

In another embodiment, the measuring transducer can be an optical sensor with a light source and a receiver, which outputs a measurement signal dependent on the received light intensity. The optical sensor is, in this case, brought in contact with the process medium by radiating light emitted from the light source on a light path extending between the light source and the receiver and through the process medium, especially through the wall of the process container.

In an additional embodiment, the measuring transducer can comprise an optically readable, sensorially active, area, which is brought in contact with the process medium.

Preferably included in the one-point calibrating are matrix effects, which result through cross sensitivities of the measured variable to be monitored to other measured variables, especially to other substances contained in the process medium.

BRIEF DESCRIPTION OF THE DRAWINGS

The invention will now be described in detail based on examples of embodiments shown in the drawing, the figures of which show as follows:

FIG. 2 is a schematic representation of an optical measuring transducer, which, for start-up, has been brought in contact with a medium in a flexible, single-use, process container.

DETAILED DISCUSSION IN CONJUNCTION WITH THE DRAWINGS

Figure 1:
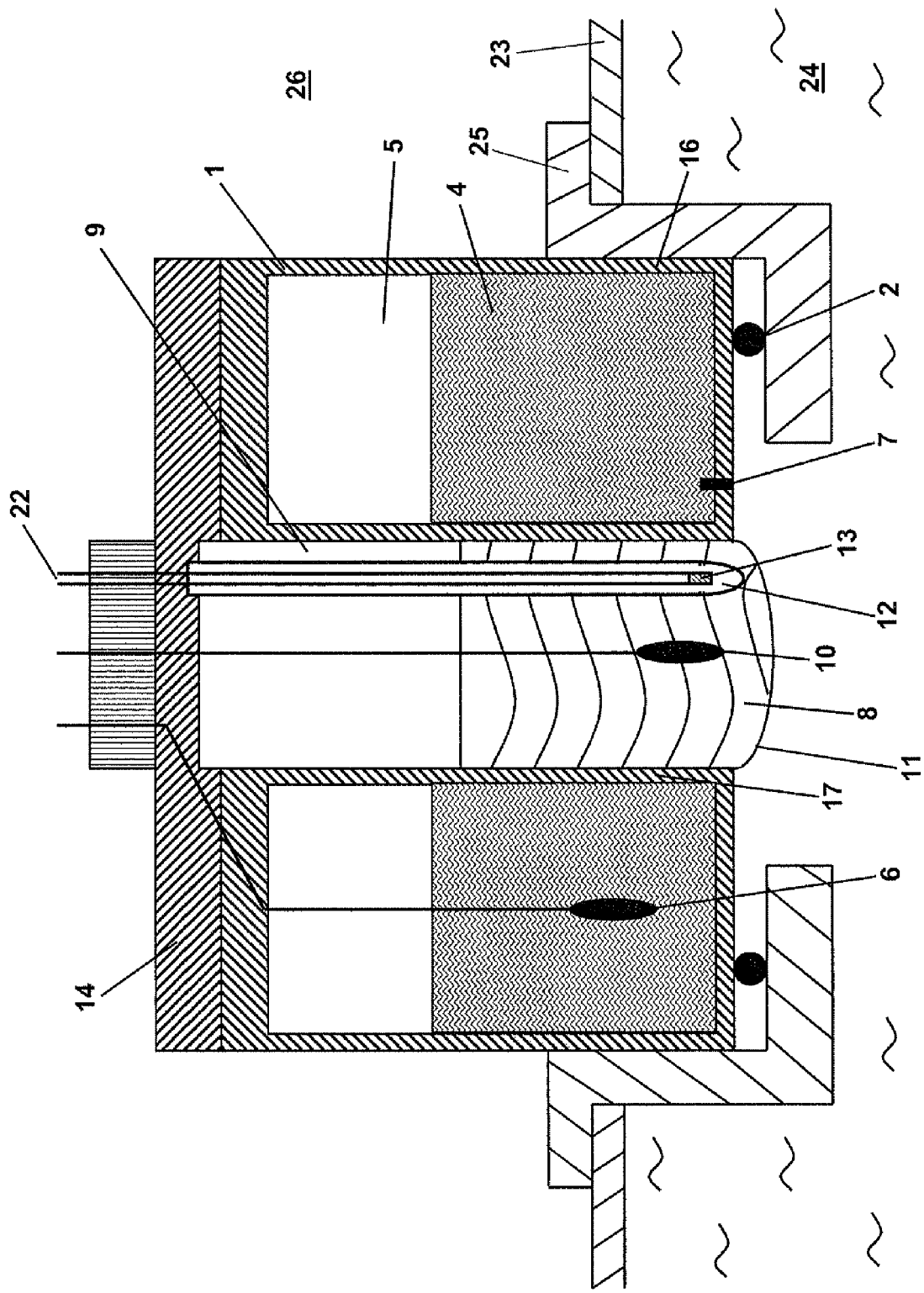
FIG. 1 is a schematic representation of a potentiometric measuring transducer, which, for start-up, has been brought in contact with a medium in a single-use, process container.

FIG. 1 shows a potentiometric measuring transducer for pH measurement. The transducer includes a housing 1 of an insulating material, which has a first chamber 5 embodied as an annular chamber, in which a reference half-cell is formed, and an essentially cylindrical second chamber 9, which is surrounded by the annular chamber and in which a measuring half cell is formed. Examples of suitable insulating material includes glass, or synthetic material, such as plastic, for example, polyetheretherketone (PEEK).

The first chamber 5 is surrounded by an outer tubular housing wall 16 and a thereto concentrically arranged, inner tubular housing wall 17 as well as by two annular housing walls, which lie opposite one another, are perpendicular to the shared cylindrical symmetry axis of the tubular housing walls 16, 17 and connect the tubular housing walls 16, 17 with one another. The second chamber 9 is formed by the inner tubular housing wall 17, which is sealed on its one end by the measuring membrane 11 and on its other end by a housing wall 14 lying opposite the measuring membrane 11.

Formed in the first chamber 5 is a reference half-cell of the potentiometric sensor. Chamber 5 contains reference electrolyte 4, into which a potential sensing electrode 6 extends. The reference electrolyte 4 can be, for example, a firm gel electrolyte or a liquid electrolyte, e.g. an aqueous 3 M KCl-solution. The potential sensing electrode 6 can be, for example, a chloridized silver wire. The remaining space of the first chamber 5 not filled by the reference electrolyte 4, also referred to as the compensation space, can contain air or also a polymer compensator, e.g. silicone foam.

In the annular housing wall bounding the first chamber 5 on the measuring membrane side, there is arranged a diaphragm 7, which serves as an electrolytic contact location, via which the reference half-cell is connected with the environment of the housing 1 for the exchange of charge carriers. In measurement operation of the measuring transducer, diaphragm 7 provides an electrical, conically conductive connection between the reference electrolytes 4 and the process medium 24 wetting the diaphragm 7. The electrolytic contact location can alternatively also be embodied as one or more bores in the housing wall or as annular gap surrounding the measuring membrane 11. The diaphragm 7 can be embodied as a disk- or pencil-shaped insert of a porous material. In the example shown here, the diaphragm 7 is embodied as a plug of microporous ceramic, for example, a micropored, zirconium dioxide ceramic. Especially, the electrolytic contact can be produced first at start-up of the potentiometric sensor, for example, by forming by means of a pointed tool, especially a pointed tool integrated in the sensor, a passageway extending between the interior of the first chamber 5 and the environment of the housing 1.

Involved in the present example in the case of the measuring membrane 11 is a pH-selective, glass membrane. Preferably, the glass membrane is made of a low-ohm glass, which provides for a rapid response, even in the case of small glass membrane areas, especially also at start-up of the sensor. The glass membrane 11 can be melted on a glass tube, which is pressed into the inner tubular housing wall 17 surrounding the second chamber 9 or adhered to the inside of the housing wall 17. The glass tube is sealed on its side lying opposite the membrane by the housing wall 14; it can also be melted or adhered on this side, or sealed by a sealing element, e.g. a plug or stopper of a polymer material. If the potentiometric sensor is embodied as an ion-selective electrode for determining an ion concentration, the measuring membrane 11 can be a polymer membrane, with or without softeners, conductive salts and/or ionophores.

The second chamber 9 contains an inner electrolyte 8, into which a potential sensing electrode 10 extends. The inner electrolyte 8 can likewise be embodied, as was the reference electrolyte 4, as a firm gel electrolyte or as an aqueous buffer solution. The non electrolyte filled compensation space of the second chamber 9 can contain air or a polymer compensator, e.g. silicone foam.

Arranged supplementally in the second chamber 9 in the example shown in FIG. 1 is a temperature sensor 13, which is arranged in a capillary tube 12 of glass or synthetic material and so comprises a temperature dependent resistor electrically insulated relative to the inner electrolyte 8. The temperature sensor 13 is only optionally present.

Electrical lines for contacting the potential sensing electrode 10 of the measuring half cell, the potential sensing electrode 6 of the reference half-cell and the temperature sensor 13 are led through the housing wall 14, which can also be embodied as potting compound, to a plug with pins 22. In given cases, the plug can be cast, at least partially, together with the potting compound. The pins 22 serve as contact locations arranged outside of the housing 1 for the potential sensing electrode 10, the reference electrode 6 and the temperature sensor 13, and, for forming a complete measuring device, can be electrically conductively connected with a measurement circuit or directly with a measurement transmitter. The potential difference between the reference half-cell and the measuring half cell depends on the value of the measured variable of the process medium 24 to be monitored, here the pH-value. It is registered and digitized as measurement signal of the measuring transducer by a measurement circuit connected with the two sensing electrodes 6, 10 and, by means of a data processing unit of the measuring device, for example, in a measurement transmitter, mapped to a measured value based on a characteristic curve stored in a memory of the measurement transmitter. In the case of pH-measuring, the registered potential difference between reference- and measuring half cell is mapped to a pH-value. Used as characteristic curve in the case of a potentiometric pH-sensor is, as a rule, a straight line, which is defined by a zero-point, or abscissa intercept, and a slope.

The housing 1 of the potentiometric measuring transducer is accommodated in a holder 25, which is fixedly connected, for example, by adhesion or welding, with a single-use, process container 25. The housing 1 can, for example, be pressed into the holder and against the sealing ring 2 via a screwed connection, so that no process medium 24 can escape from the interior of the process container 23 into the environment 26. The region surrounded by the sealing ring 2, including the diaphragm 7 and the measuring membrane 11, is the immersion region of the potentiometric measuring transducer 1 coming in contact with the process medium 24.

FIG. 2 shows schematically at start-up an with an optical measuring transducer 33 in contact with process medium 31 in a flexible, single-use, process container, for example, a bag-fermenter 30. The measuring transducer 33 can serve, for example, for measuring the pH-value, the dissolved oxygen content, the CO2-content or the temperature of the process medium 31. For accommodating the measuring transducer 33, the bag-fermenter 30 possesses a holder 34 fixedly connected, e.g. by adhesion or welding, with the bag wall. The tubular measuring transducer housing 35 of the measuring transducer 33 is inserted into the holder and sealed, for example, by means of O-ring sealing elements (not shown in detail) against the exit of process medium 31 into the environment. Arranged in the measuring transducer housing 35 is an at least partially transparent inner tube 36, especially transparent for measuring radiation of the optical measuring transducer 33. Tube 36 has on its front end a membrane 37, which, for performing a measuring, especially at start-up of the measuring transducer 33, is brought in contact with the process medium 35. Membrane 37 contains a substance, which, in contact with the process medium in the case of exciting with radiation of a measuring wavelength, radiates a fluorescence signal, whose intensity depends on the variable to be monitored for the process medium, for example, pH-value, oxygen content, CO2-content or temperature. The substance can alternatively also possess an absorption dependent on the measured variable to be monitored. The measuring radiation is radiated via light conductor 38 to the membrane 37 and the fluorescence signal, or the measuring radiation changed by interaction with the substance, e.g. interaction in terms of absorption, is fed via the light conductor 38 to a measurement circuit (not shown), which includes an optoelectronic element for detection of the signal intensity. The measurement circuit transduces the fluorescence intensity, or the measurement radiation intensity, into an electrical, measuring transducer signal, which is output to a superordinated unit, for example, a measurement transmitter, connected with the measuring transducer 33 for forming a measuring device. The measurement transmitter includes a data processing unit, which has at least one processor and at least one data memory. The data processing unit maps, by means of a characteristic curve stored in the data memory, the sensor signal to a measured value of the measured variable to be monitored.

A method for start-up of the sensor according to one of the two examples of embodiments previously described at length or according to one of the above described, additional embodiments will now be described in detail.

The measuring transducer is first provided in the previously described manner for registering measured values. After providing the measuring transducer on or in a container wall of the single-use container, this can with the integrated measuring transducer be subjected to a sterilization, for example, by irradiation with gamma-radiation. Thereafter, the sterilized container with the measuring transducer is stored prior to its use. When the single-use container is finally needed for performing, for example, a biotechnological method, the measuring transducer is readied for operation. For this, the measuring transducer is connected with a superordinated unit, in order to form a measuring device. For example, a potentiometric measuring transducer according to FIG. 1 is connected with the superordinated unit via the plug 22. The optical measuring transducer shown in FIG. 2 is connected, via a connector (not shown) of the light conductor 38, with the measurement circuit and a data processing unit. The superordinated unit possesses a data processing unit for processing the measuring signals output by the sensor. The evaluation circuit is embodied, in manner known per se, to associate with a measurement signal of the sensor, based on a characteristic curve stored in its memory, a measured value of the measured variable to be monitored by the sensor. The characteristic curve can be, for example, a straight line, which is defined by its zero-point, or axial intercept, and a slope. The following explanations relate to the potentiometric measuring of the pH-value, but hold, however, in analogous manner for measuring other measured variables by means of optical, electrochemical or other sensors.

To the process container is first fed a first process medium. Preferably, the first process medium is a substance, which has a known pH-value. The pH-value of the first process medium can have been ascertained, for example, by way of an earlier performed, reference measurement. Frequently, also process media are applied, which are subject to a strict specification. This is true, for example, for feeding solutions in biotechnological processes. The feeding solutions are exactly specified as regards pH-value on tolerances of 0.1 to 0.05 pH. When an electrochemical connection between the reference electrolytes of the measuring transducer and the first process medium is produced, the first process medium, for example, the feeding solution, can be utilized for performing a one-point calibrating of the measuring device.

For performing the one-point calibrating, the pH-value of the process medium, for example, the feeding solution, is registered with the measuring device and mapped to a measured value. Based on comparison between the known actual pH-value of the feeding medium and the pH-value ascertained based on the measuring transducer signal, the characteristic curve is adjusted. In the present case of a line, is thus, the zero-point, or the axial intercept, is adjusted. Alternatively, it is also possible to compare the measurement signal of the pH-sensor with a theoretical signal calculated from the known pH-value of the process medium, for example, based on the Nernst-equation, and based on this comparison, to fit the zero-point, or the abscissa intercept, of the characteristic curve.

In the case of little chemically, mechanically or thermally loaded pH-sensors, the slope lies in the range of 58-59 mV/pH, i.e. near the theoretical value of 59.2 mV/pH at 25° C. Since the zero-point of the described pH-sensors with a pH-sensitive glass membrane lies, as a rule, at pH=7, error from an insufficiently calibrated slope first becomes noticeable at pH-values differing strongly from pH=7. An error from an insufficiently calibrated zero-point acts, in contrast, over the total pH-measuring range. Since especially in biotechnological processes, in which microorganisms are used, as a rule, the pH-value is kept in the range of pH=6 to 8, an insufficiently calibrated zero-point is here the main source of error. A one-point-calibration in the here described manner is therefore sufficient in such applications, in order to eliminate the error most affecting the accuracy of measurement.

After the one-point calibrating, other process media can be introduced into the single-use container, especially in one of the described biotechnological applications requiring microorganisms.

The invention claimed is:

1. A method for start-up of a measuring device, which is embodied to monitor by means of at least one measuring transducer in contact with the interior of a process container, a measured variable of a medium contained in the process container, wherein, for ascertaining a measured value, at least one measurement signal of the measuring transducer is mapped to a measured value of the measured variable according to a predetermined characteristic curve, wherein the method comprises the steps of:

introducing a process medium into the process container;

bringing the measuring transducer in contact with the process medium; and performing a one-point calibrating of the measuring device based on a measurement signal registered by the measuring transducer in the process medium or a measured value derived therefrom based on the characteristic curve, wherein:

the process medium is a feeding medium for microorganisms of a biotechnological process, whose value of the measured variable to be monitored by the measuring transducer is known.

2. The method as claimed in claim 1, wherein:

said one-point calibrating includes the steps of:

registering by means of the measuring device a measured value of the measured variable of the process medium as a current calibration measured value; and updating the predetermined characteristic curve (according to which a measurement signal of the measuring transducer is mapped to a measured value) stored in a memory associated with the measuring device based on the current calibration measured value.

3. The method as claimed in claim 1, wherein:

the characteristic curve is a straight line; and the straight line is corrected based on the current calibration measured value of the zero-point (axial intercept).

4. The method as claimed in claim 1, wherein:

the process medium is a feeding medium for microorganisms of a biotechnological process, whose chemical composition is known.

5. The method as claimed in claim 1, wherein:
the measured variable is one of a pH-value, conductivity, or a concentration of a substance.

6. The method as claimed in claim 5, wherein:
said concentration of a substance is one of: a concentration of a dissolved gas or of a type of ion or a concentration of a substance relevant for a biotechnological process to be monitored.

7. The method as claimed in claim 1, wherein:
the process container is one of:
a single-use container, a bag-fermenter, a hose, or a tubular connection, for application in a biotechnological process.

8. The method as claimed in claim 1, wherein:
the measuring transducer is a potentiometric sensor with a measuring half cell and a reference half-cell;
the sensor has an immersion region, which includes a membrane of a said measuring half cell sensitive for the measured variable to be monitored and an electrolytic contact location for providing electrolytic contact between the reference half-cell and the process medium; and
the measuring transducer is brought in contact with the process medium by immersing the immersion region in the process medium.

9. The method as claimed in claim 1, wherein:
the measuring transducer is an optical sensor with a light source and a receiver, which outputs a measurement signal dependent on a light intensity received by the receiver; and
the optical sensor is brought in contact with the process medium by radiating light emitted by the light source on a light path extending between the light source and the receiver through the process medium.

10. The method as claimed in claim 9, wherein:
the light is emitted by the light source on a light path extending between the light source and the receiver through the process medium and a wall of the process container.

11. The method as claimed in claim 1, wherein:
supplementally taken into consideration in the one-point-calibration are matrix effects, which result through cross sensitivities of the measured variable to be monitored to other measured variables.

\* \* \* \* \*